(12) United States Patent
Alferness et al.

(10) Patent No.: US 7,182,772 B2
(45) Date of Patent: *Feb. 27, 2007

(54) CONSTRICTION DEVICE INCLUDING FIXATION STRUCTURE

(75) Inventors: Clifton A. Alferness, Redmond, WA (US); Robert Barry, Kirkland, WA (US); Clint Finger, Bellevue, WA (US); Leslie Snyder, Kirkland, WA (US); Jenni Rimbaugh, Bothell, WA (US)

(73) Assignee: Spiration, Inc., Redmond, WA (US)

( * ) Notice: Subject to any disclaimer, the term of this patent is extended or adjusted under 35 U.S.C. 154(b) by 190 days.

This patent is subject to a terminal disclaimer.

(21) Appl. No.: 10/287,189

(22) Filed: Nov. 4, 2002

(65) Prior Publication Data

US 2003/0069488 A1   Apr. 10, 2003

Related U.S. Application Data

(63) Continuation of application No. 09/902,821, filed on Jul. 10, 2001, now Pat. No. 6,491,706.

(51) Int. Cl.
*A61B 17/12* (2006.01)
(52) U.S. Cl. .................................. 606/157; 600/37
(58) Field of Classification Search ................ 606/155, 606/156, 157, 213
See application file for complete search history.

(56) References Cited

U.S. PATENT DOCUMENTS

| | | | | |
|---|---|---|---|---|
| 5,063,913 A | * | 11/1991 | Nyi | 602/20 |
| 5,578,047 A | * | 11/1996 | Taylor | 606/157 |
| 5,976,158 A | * | 11/1999 | Adams et al. | 606/140 |
| 5,984,963 A | * | 11/1999 | Ryan et al. | 623/1.11 |
| 6,030,392 A | | 2/2000 | Dakov | |
| 6,280,452 B1 | | 8/2001 | Mears | |
| 6,328,689 B1 | * | 12/2001 | Gonzalez et al. | 600/37 |
| 6,416,554 B1 | * | 7/2002 | Alferness et al. | 623/23.65 |
| 6,491,706 B1 | * | 12/2002 | Alferness et al. | 606/157 |
| 6,589,161 B2 | * | 7/2003 | Corcoran | 600/37 |
| 6,632,239 B2 | * | 10/2003 | Snyder et al. | 606/213 |
| 6,790,172 B2 | * | 9/2004 | Alferness et al. | 600/37 |
| 6,860,847 B2 | * | 3/2005 | Alferness et al. | 600/37 |

* cited by examiner

Primary Examiner—Anhtuan T. Nguyen
Assistant Examiner—Darwin P. Erezo
(74) Attorney, Agent, or Firm—Knobbe, Martens, Olson & Bear LLP

(57) ABSTRACT

A constriction device that constricts body tissue includes fixation structures for fixing the device on constricted body tissue. The device includes an elongated sleeve including an inner surface and opposed opened ends. The device is formed from expandable or elastic material so that when in an expanded condition, body tissue to be constricted may be received therein and thereafter, when released from the expanded condition, the body tissue is constricted by the device. The fixation structures include a plurality of fixation elements on the inner surface of the sleeve that grasp the body tissue upon release of the sleeve from the expanded condition to fix the device on the constricted tissue.

13 Claims, 6 Drawing Sheets

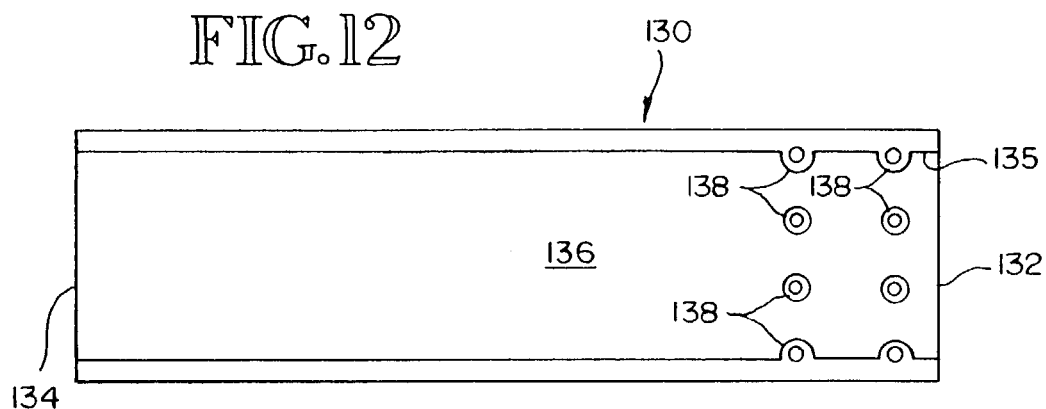
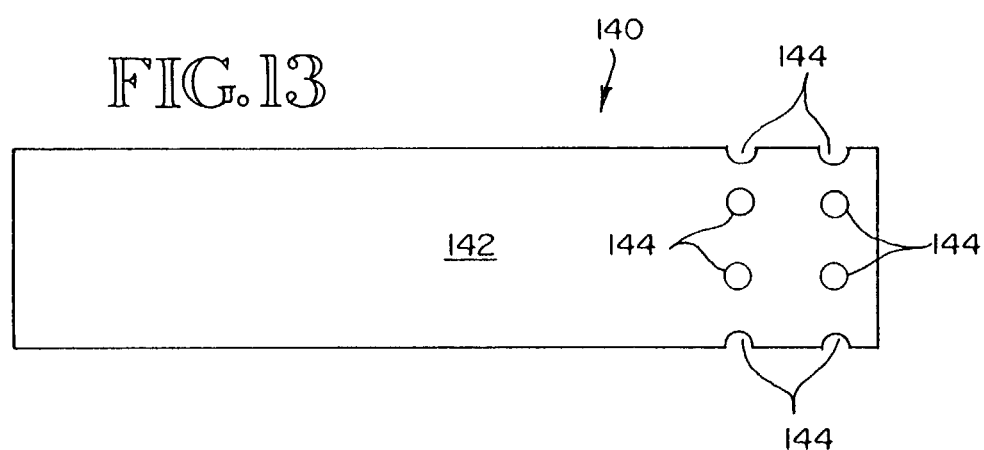
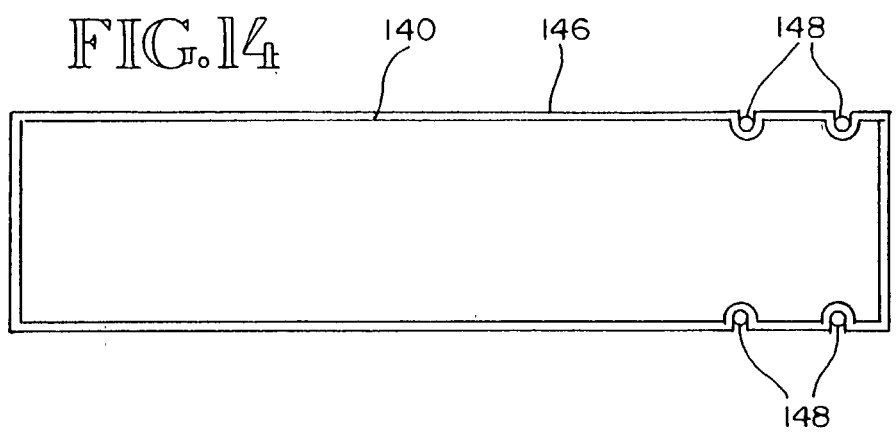

CONSTRICTION DEVICE INCLUDING FIXATION STRUCTURE

RELATED APPLICATION

This application is a continuation of application Ser. No. 09/902,821, filed Jul. 10, 2001, now U.S. Pat. No. 6,491,706.

BACKGROUND OF THE INVENTION

The present invention is generally directed to a constricting device that constricts body tissue. The present invention is more particularly directed to a constricting device that includes fixation structures to preclude the constricting device from being dislodged from the constricted body tissue. The present invention is still further directed to such a device which is viewable under X ray fluoroscopy.

Constriction devices have been contemplated for constricting body tissue. Such devices have been considered for use, for example, in tissue resection procedures and in treating pulmonary disease.

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991 COPD was the fourth leading cause of death in the United States and had increased 33% since 1979.

COPD affects the patient's whole life. It has three main symptoms: cough; breathlessness; and wheeze. At first, breathlessness may be noticed when running for a bus, digging in the garden, or walking up hill. Later, it may be noticed when simply walking in the kitchen. Over time, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled β-agonists. For those patients who respond poorly to the foregoing or who have persistent symptoms, Ipratropium bromide may be indicated. Further, courses of steroids, such as corticosteroids, may be required. Lastly, antibiotics may be required to prevent infections and influenza and pneumococcal vaccines may be routinely administered. Unfortunately, there is no evidence that early, regular use of pharmacotherapy will alter the progression of COPD.

Lung transplantation is also an option. Today, COPD is the most common diagnosis for which lung transplantation is considered. Unfortunately, this consideration is given for only those with advanced COPD. Given the limited availability of donor organs, lung transplant is far from being available to all patients.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopped remitting for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life.

Improvements in pulmonary function after LVRS have been attributed to at least four possible mechanisms. These include enhanced elastic recoil, correction of ventilation/perfusion mismatch, improved efficiency of respiratory musculature, and improved right ventricular filling.

The improvements in pulmonary function resulting from LVRS cannot be ignored. However, the surgery is very invasive and fraught with complications. Among the complications is the potential for lung air leaks. Lung tissue is very thin, and fragile hence difficult to suture together. After a lung portion is sectioned and removed, the remaining lung is most often restructured with suture staples. In about thirty percent (30%) of the cases, the difficulty with suturing lung tissue results in air leaks. Treatment for such air leaks depends upon their severity and often, in the most serious cases, requires further open chest surgery.

Air leaks in lungs can be caused by other causes. With increasing age, a patient may develop a weakened section of lung which may then rupture due to an extreme pressure differential, such as may result from simply a hard sneeze. AIDS patients can suffer from air leaks in their lungs. Air leaks in lungs can further be caused by a puncture from a broken rib or a stab wound.

The invention disclosed and claimed in copending U.S. application Ser. No. 09/534,244, incorporated herein by reference, provides an improved therapy for treating COPD and air leaks in lungs. The therapy includes a constriction device which, when deployed on a lung, suppresses air leaks in the lung tissue without requiring any suturing of the effected lung tissue. Still further, by constricting a large enough portion of a lung with the device, lung volume reduction with the concomitant improved pulmonary function may be obtained without the need for any suturing of lung tissue at all.

The lung constriction device includes a jacket or sheath of flexible material configured to cover at least a portion of a lung. The jacket has a pair of opened ends to permit the lung portion to be drawn into the jacket. The jacket is dimensioned to constrict the lung portion after the lung portion is drawn therein. The lung constriction device is preferably formed of expandable, such as elastic, material for receiving the lung tissue while the device is in an expanded or enlarged condition, and then contractible about the lung portion upon release of the expanded condition for constricting the lung tissue.

An important aspect of the device and method disclosed in U.S. application Ser. No. 09/534,244 is the ability to sever the constricting device intermediate its ends. This allows a significant portion of the constricted lung tissue to be removed altogether while permitting a portion of the constricting device to remain in the body for continued suppression of air leaks and maintenance of the remaining lung tissue integrity.

Devices and methods similar to those disclosed in U.S. application Ser. No. 09/534,244 may be employed to advantage in other and different procedures such as in general resection procedures and for body tissue other than lung tissue. Resection procedures are commonly performed for such body tissue as, for example, atrial appendage tissue, ovarian tissue, gall bladder tissue, pancreatic tissue, appendix tissue and spleen tissue. Resection procedures may be required to treat cancer, organ damage, or organ disease, for example.

U.S. application Ser. No. 09/534,244 also discloses and claims various methods and apparatus for deploying the constricting device on body tissue such as lung tissue. One apparatus and method contemplates mechanically expanding the device in a transverse dimension while physically pulling the tissue to be constricted into the device.

Another method contemplates mounting the device over a vacuum chamber and pulling the tissue into the vacuum chamber by engaging the tissue with an opened end of the chamber and then drawing a vacuum in the chamber. This draws the tissue into the chamber. Then, the chamber is withdrawn from the device, leaving the tissue constricted in the device.

A further method contemplates inserting the device into a vacuum chamber and sealing the opened end of the chamber to the device. The opened end of the chamber and the tissue are then brought into sealing engagement. A vacuum is next pulled in the chamber and the device to pull the tissue into the device and chamber. Once the tissue is within the device, the chamber is removed from over the device leaving the tissue constricted in the device.

Although various methods and apparatus have been conceived for effectively deploying constriction devices on body tissues, the constriction devices, over time, may become dislodged due to the nature of the soft tissue on which they are deployed. More specifically, soft body tissue has a tendency to expand at the proximal end of the device causing longitudinal slippage of the device on the body tissue. This may eventually lead to the device slipping totally free from the tissue. Hence, there is a need for additional constriction device structure for fixing the device on the tissue.

In addition, some contemplated uses of the constriction devices, such as in effecting a reduction in lung volume, require that the device remain on the tissue for an indeterminate period of time. Once the patient has recovered from the deployment procedure, it would be helpful to be able to determine that the device has remained in position. Hence, there is a need for such a device to be visible by the physician in some manner long after the deployment procedure has taken place.

The present invention addresses these needs. It provides a constriction device having positive fixation structure for maintaining the constriction device deployed on the body tissue. The present invention further renders it possible to determine the position of the device within the body to permit medical personnel to confirm that the device has remained in place and that it continues to be effective. In accordance with particular aspects of the present invention, it is the fixation structure which also renders it possible to determine the position of the device.

SUMMARY OF THE INVENTION

The invention provides a constriction device that constricts body tissue and which includes fixation structure for maintaining the device on constricted body tissue. The device includes an elongated sleeve, the sleeve including an inner surface and opposed opened ends and being formed from expandable material to receive therein, when in an expanded condition, body tissue to be constricted and to constrict the body tissue therein when released from the expanded condition. The device further includes a plurality of fixation elements on the inner surface of the sleeve that grasp the body tissue upon release of the sleeve from the expanded condition. The fixation elements may include radio opaque material, such as, for example, material visible under X ray fluoroscopy.

The fixation elements may be adjacent to one of the opposed openings and arranged in a side-by-side relation to grasp the body tissue between adjacent fixation elements when the sleeve is released from the expanded condition. The fixation elements may further include barbs to further assist in fixing the device on the constricted body tissue.

The device may be further configured so that the sleeve further includes a longitudinal side wall extending between the opposed opened ends. The fixation elements may be integral to the longitudinal side wall or adhered to the inner surface of the sleeve.

The fixation elements include inner surfaces that engage the body tissue. The inner surfaces of the fixation elements may be roughened surfaces to further assist in grasping the constricted body tissue. The fixation elements may also be configured to include a major dimension extending along the longitudinal dimension of the sleeve.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

FIG. 12 is a sectional side view of another constriction device embodying the present invention;

FIG. 13 is a side view of a mandrel which may be used in making the constriction device of FIG. 13;

FIG. 14 is a sectional side view of the mandrel of FIG. 13 at an intermediate stage in the making of the constriction device of FIG. 13.

DETAILED DESCRIPTION

Figure 1:
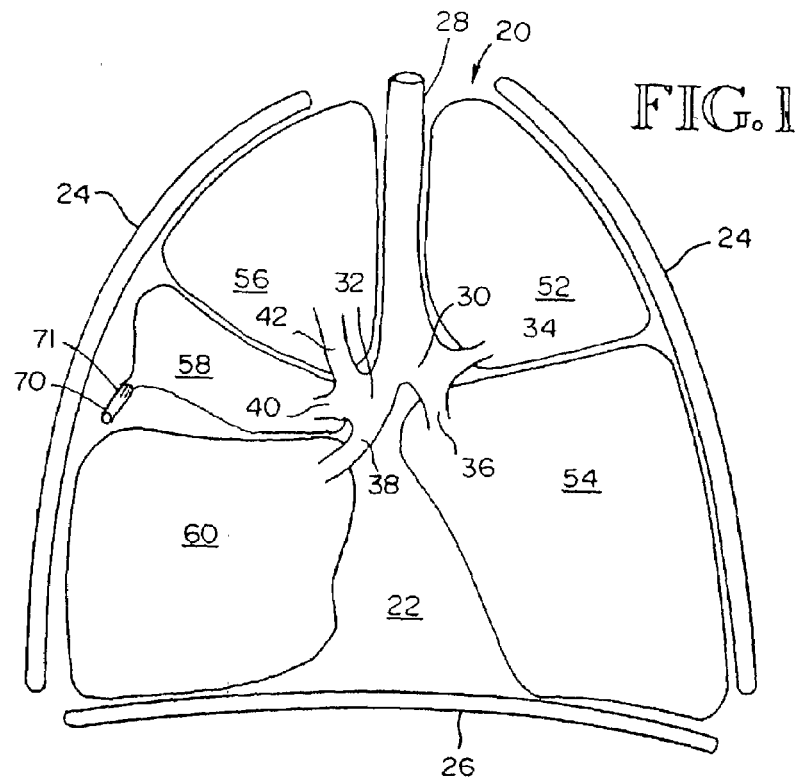
FIG. 1 is a simplified sectional view of a thorax illustrating a respiratory system having a constricting device embodying the present invention deployed on a portion of a lung to effect lung volume reduction.

Referring now to FIG. 1, it is a sectional view of a respiratory system 20. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, and the bronchial branches 34, 36, 38, 40, and 42. The respiratory system 20 further includes left lung lobes 52 and 54 and right lung lobes 56, 58, and 60. Each bronchial branch communicates with a respective different portion of a lung lobe, either the entire lung lobe or a portion thereof.

A healthy respiratory system has an arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air to an inflated condition. When the individual exhales, the diaphragm returns to its original arched condition to decrease the volume of the thorax. The decreased volume of the thorax causes a positive pressure within the thorax which in turn causes exhalation of the lung lobes.

FIG. 1 also shows a constriction device 70 embodying the present invention deployed on lobe 58. The device 70 is configured as a sleeve or sheath formed of a sheet of flexible or elastic biocompatible material. The material may be formed from silicone rubber, polyurethane, expanded polytetraflouroethylene, polyester and polyurethane, or nylon and polyurethane, for example. It may alternatively be flexible but nonexpandable formed from nylon, polytetraflouroethylene, or polyester, for example. If the sleeve is expandable, it may more specifically be formed from a sheet or fabric of 70% nylon and 30% polyurethane. The sleeve is preferably opened at both ends and may be generally cylindrical in configuration.

As will be seen subsequently, in accordance with the preferred embodiment of the present invention, the sleeve is applied to the lung lobe while in an expanded condition. This may be accomplished by expanding the sleeve with a first vacuum and then pulling the lung portion into the sleeve with a second vacuum. When the lung portion is within the sleeve, the expansion of the device is released. With the expansion released, the sleeve is permitted to contract or collapse about the lung portion to constrict the lung portion.

The device 70 may be employed, for example, to suppress air leakages in lungs. It may also find use to advantage in constricting a lung portion suffering from COPD to simulate or achieve lung volume reduction. All of the beneficial effects of lung volume reduction surgery may be realized and, most importantly, without requiring suturing of lung tissue.

In accordance with the present invention, the constriction device 70 includes a plurality of coated strips 71 on the outer surface of the device 70. The strips are formed from gold, for example, to render the device visible under X ray fluoroscopy. This makes it possible for the physician to confirm at a later time that the device has maintained its position on the lung tissue 58.

Figure 2:
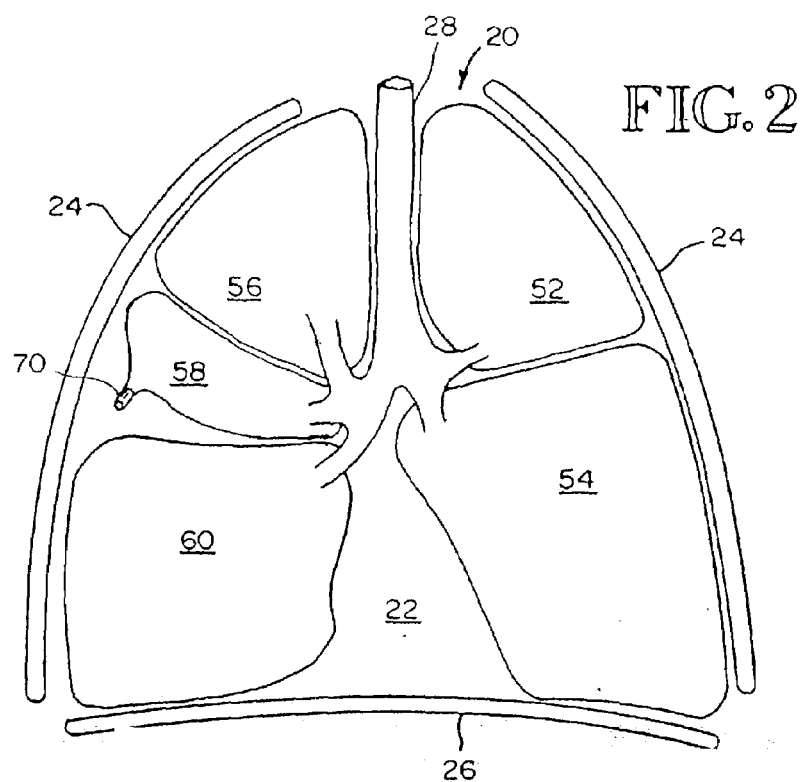
FIG. 2 is a sectional view similar to FIG. 1 but illustrating the respiratory system after the constricted lung portion has been resectioned.

FIG. 2 shows the respiratory system 20 after the constricted lung portion has been resectioned. The device 70 is preferably formed of severable material, such as, any of the materials previously described. This enables the device 70 to be severed or cut intermediate its ends with a suitable bladed instrument to resection the lung lobe 58. The portion of the device 70 remaining on the lobe 58 continues to constrict the lung tissue therein to form an effective seal from leakage. The strips 71 are coated on the device 70 to extend from the proximal end of the device. This enables at least portions of the strips 71 to remain after resectioning to permit future confirmation that the device 70 remains in place on the lung tissue. Hence, lung volume reduction is rendered an available treatment while negating the need of conventional lung sectioning and suturing thus avoiding the potentially severe complications which accompany those procedures.

Figure 3:
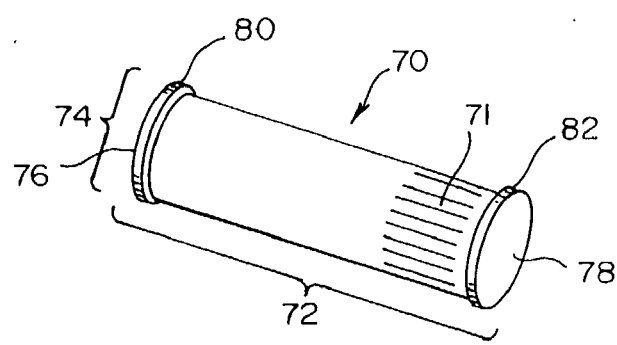
FIG. 3 is a perspective view illustrating a constricting device embodying the present invention.

FIG. 3 illustrates the constricting device 70 in greater detail. The device 70 is a generally cylindrical sleeve having a longitudinal dimension 72 and a transverse dimension 74. As previously mentioned, the device 70 is preferably formed of an elastic material permitting the device to expand in the longitudinal dimension and more importantly in the transverse dimension. The device 70 has opposed opened ends 76 and 78. The device may further include at each end 76 and 78 an integral rim 80 and 82 respectively.

The strips 71 of X ray opaque material extend longitudinally along the outer surface of the device 70. The strips 71 also extend from the opening 78 which, when deployed on the lung tissue 58, is at the proximal end of the device. This enables the strips 71 to remain on the device within the patient's body even though the device may be severed for resectioning the lung tissue or any other tissue on which the device 70 is deployed.

Figure 4:
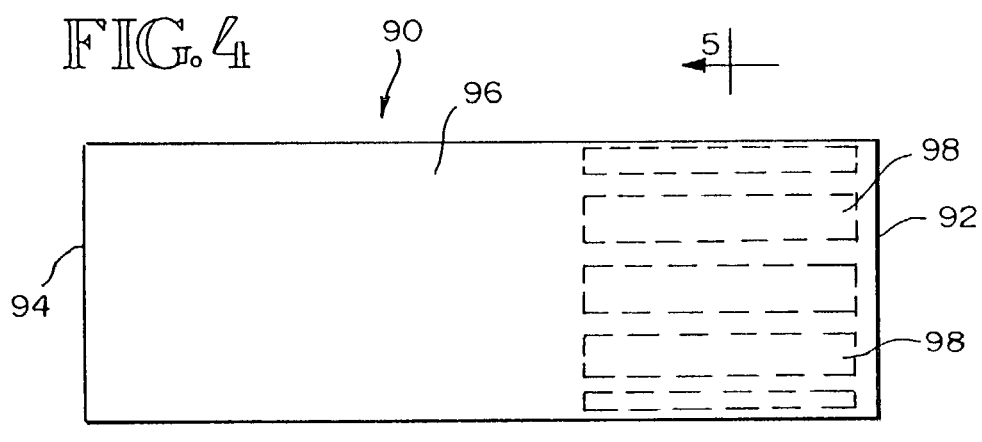
FIG. 4 is a side view of a construction device including X ray visible elements in accordance with another embodiment of the present invention.
Figure 5:
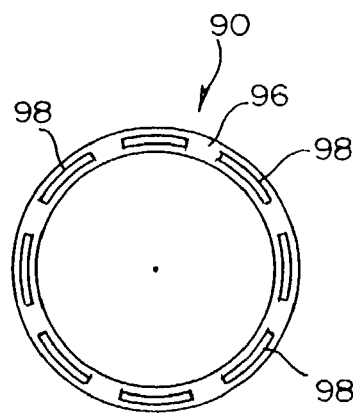
FIG. 5 is a sectional view taken along lines 5—5 of FIG. 4.

FIGS. 4 and 5 illustrate another constriction device 90 embodying the present invention. Like the device 70, the device 90 is a sleeve, generally cylindrical in configuration, having opposed opened ends 92 and 94. Embedded within the longitudinal side wall 96 of the device 90, and extending longitudinally there along, are a plurality of strips 98 of X ray opaque material. The strips 98, again, may be formed of gold, for example, or any other material known in the art which is visible under X ray fluoroscopy.

Like the strips 71 of the device 70, the strips 98 of the device 90 extend from an opened end 92. By extending longitudinally, the strips 98 permit the device 90 to expanding transversely or radially outwardly during the deployment of the device 90. Once the device collapses about the tissue to be constricted, the strips may be seen under X ray fluoroscopy to confirm its position with the patient's body.

Figure 6:
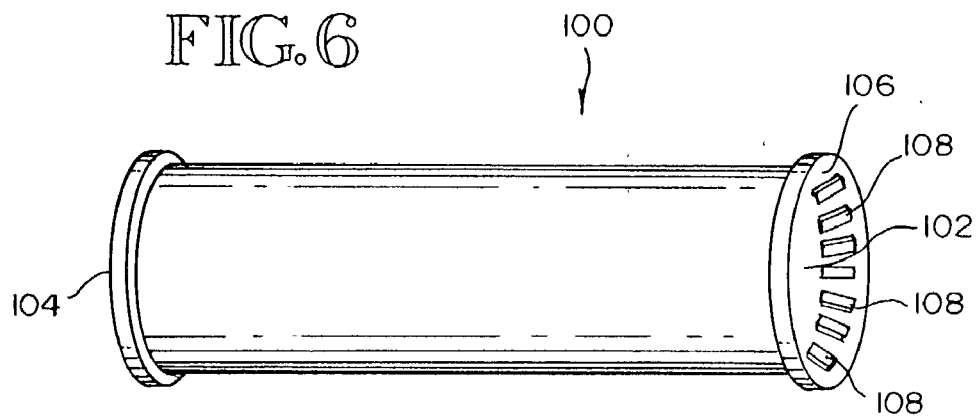
FIG. 6 is a perspective view of another construction device embodying the present invention having fixation elements on an inside surface thereof wherein the fixation elements may be formed of material visible under X ray fluoroscopy in accordance with the present invention.

FIG. 6 illustrates another constriction device 100 embodying the present invention. The device 100 again is a generally cylindrical sleeve having opposed opened ends 102 and 104. Adjacent the opened end 102 and on the inner surface 106 of the sleeve are a plurality of fixation elements 108. In accordance with this embodiment, the fixation elements are elongated bars arranged adjacent each other and circumscribing the opening 102. The fixation elements are closely spaced. When the device 100 is expanded to receive the tissue to be constricted, the tissue at least partially fills the spaces between adjacent fixation elements. Then, when the device 100 is permitted to collapse about the tissue to be constricted, adjacent fixation elements move toward each to grasp the tissue. This provides positive fixation of the device on the constricted tissue and serves to resist migration or movement of the device in a longitudinal direction to maintain the device in a fixed position on the tissue.

The fixation elements 108 are preferably formed of an X ray opaque material such as gold or stainless steel, for example. Again, this makes it possible to discern the position of the device 100 under X ray fluoroscopy. Hence, in accordance with this embodiment, the fixation elements served a dual purpose, fixing the device 100 on the constricted tissue and rendering at least a portion of the device visible under X ray fluoroscopy.

Figure 7:
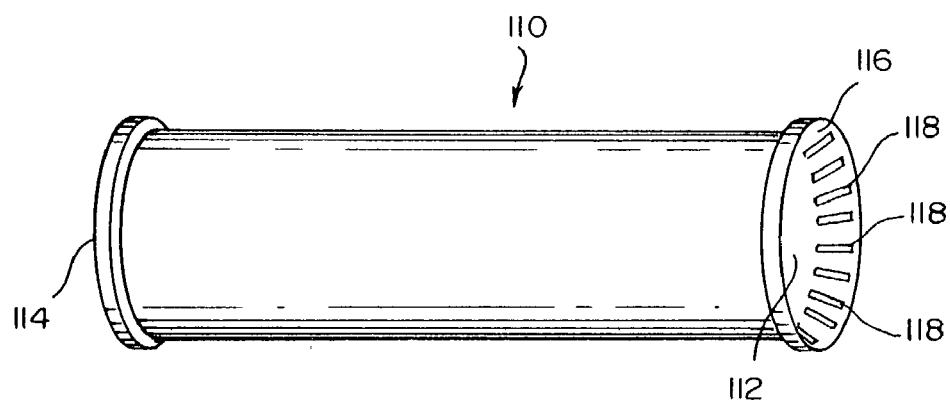
FIG. 7 is a perspective view of another constriction device embodying the present invention.

FIG. 7 illustrates another constriction device 110 embodying the present invention. The device 110 again is a generally cylindrical sleeve having opposed opened ends 112 and 114. Adjacent the opened end 112 and on the inner surface 116 of the sleeve are a plurality of fixation elements 118. In accordance with this embodiment, the fixation elements take the form of wires or elongated pins. The fixation elements are arranged adjacent each other and circumscribe the opening 112. The fixation elements are closely spaced and function in the same manner as the fixation bars 108. Hence, when the device 110 is expanded to receive the tissue to be constricted, the tissue at least partially fills the spaces between adjacent pins. Then, when the device 110 is collapsed about the tissue to be constricted, adjacent pins move toward each to grasp the tissue. This again provides positive fixation of the device on the constricted tissue.

Again, the pins 118 are preferably formed of an X ray opaque material such as gold or stainless steel, for example. This makes it possible to discern the position of the device 100 under X ray fluoroscopy. Hence, in accordance with this embodiment, the pins serve the dual role of fixing the device 110 on the constricted tissue and rendering at least a portion of the device visible under X ray fluoroscopy.

Figure 8:
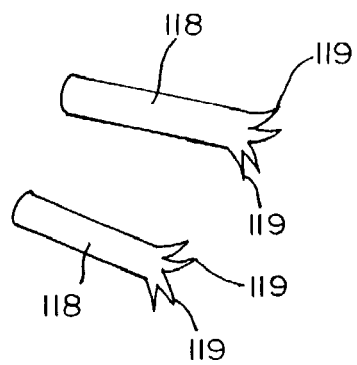
FIG. 8 is a perspective view of fixation elements which may be employed in accordance with the present invention.

As may be best seen in FIG. 8, the pins 118 may be provided with projecting barbs 119. The barbs 119 promote the grasping of the constricted tissue and provide additional gripping action for maintaining the device 110 in a fixed position once deployed.

Figure 9:
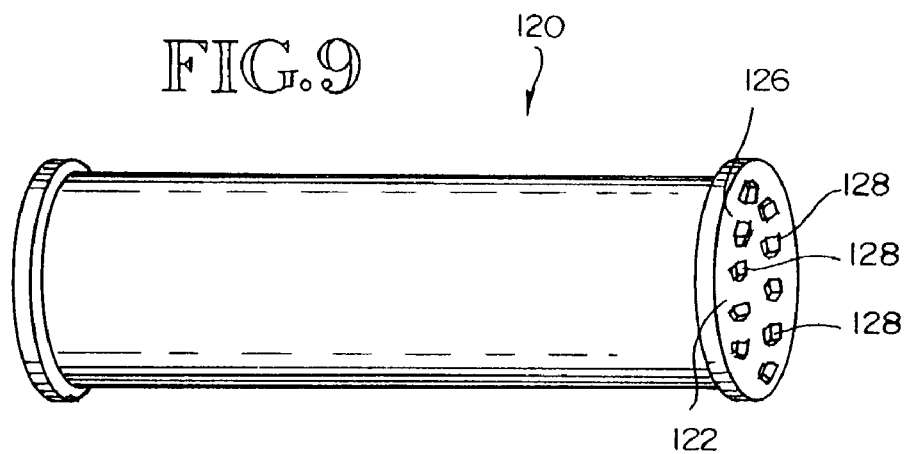
FIG. 9 is a perspective view of another constriction device embodying the present invention.

FIG. 9 illustrates still another constriction device 120 embodying the present invention. Again, the device 120 is a generally cylindrical sleeve having opposed opened ends 122 and 124. Adjacent the opened end 122 and on the inner surface 126 of the sleeve are a plurality of fixation elements 128. In accordance with this embodiment, the fixation elements are generally square shaped pads arranged in rows adjacent each other and circumscribing the opening 122. As in the previous embodiments, the fixation elements are closely spaced. As may be best seen in FIG. 10, when the device 120 is expanded to receive the tissue 58 to be constricted, the tissue at least partially fills the spaces, such as space 129, between adjacent fixation elements. Then, when the device 120 is permitted to collapse about the tissue to be constricted as may best be seen in FIG. 11, adjacent fixation elements 128 move toward each other to grasp the tissue. This again provides positive fixation of the device on the constricted tissue and serves to resist migration or movement of the device in a longitudinal direction to maintain the device in a fixed position on the tissue.

The fixation elements 128 are again preferably formed of an X ray opaque material such as gold or stainless steel, for example. Again, this makes it possible to discern the position of the device 100 under X ray fluoroscopy. Hence, the fixation elements 128 fix the device 120 on the constricted tissue and render at least a portion of the device 120 visible under X ray fluoroscopy.

Figure 10:
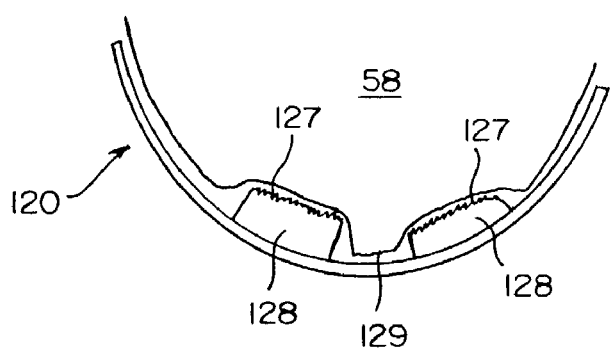
FIG. 10 is a partial end view of the constriction device of FIG. 10 illustrating the manner in which the fixation elements function prior to the collapse of the constriction device.
Figure 11:
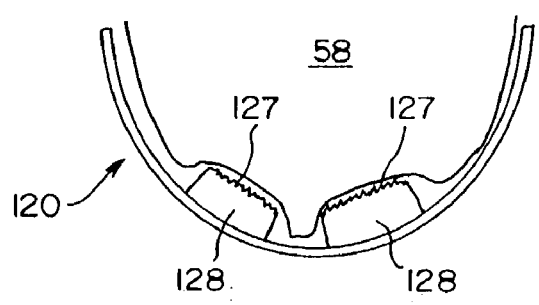
FIG. 11 is another partial end view of the constriction device of FIG. 10 illustrating the manner in which the fixation elements grasp the constricted tissue upon collapse of the constriction device.

As may also be noted in FIGS. 10 and 11, the fixation elements 128 may be provided with a roughened surface 127. This further promotes gripping of the tissue 58 by the fixation elements 128.

FIG. 12 illustrates another constriction device 130 embodying the present invention. Again, the device 130 is a generally cylindrical sleeve having opposed opened ends 132 and 134. In accordance with this embodiment, the fixation elements are integral to and within the longitudinal side wall 136 of the device 130. More specifically, the fixation elements take the form of integral protrusions 138 extending inwardly from the inner surface 135 of the device 130. The protrusions 138 serve to grasp the constricted tissue when the device is permitted to collapse about the tissue.

FIG. 13 illustrates a mandrel 140 which may be used in making the constriction device 130 of FIG. 12. The mandrel 140 is generally cylindrical in configuration and includes on its outer surface 142 a plurality of semispherical indentations or divots 144.

The device 130 may be made by using the mandrel 140 in a dipping process. Here, the mandrel is dipped into a liquid material, such as liquid silicone rubber which is elastic when hardened. After at least two such dips, the assembly of FIG. 13 will appear as shown in FIG. 14. The mandrel 140 is now covered by a silicone rubber film. Into each semispherical divot of the film a hardened or solid sphere 148 is placed. Then, the assembly of FIG. 14 is once again subjected to multiple additional dips into the liquid silicone rubber until the side wall of the device 130 is built up to a suitable thickness, such as, for example, 0.015 inches. The resulting film is then permitted to harden. Once hardened, the end panels are cut away to form the opposed opened ends 132 and 134 and the film is removed from the mandrel. What remains is the device 130 of FIG. 12.

Preferably, the solid spheres 148 are formed of a material opaque to X rays. Such a material may, for example, be gold or stainless steel. This renders the device 130 at least partially visible under X ray fluoroscopy. As a result, the device 130 is provided with a fixation structure in the form of integral protrusions 138 while also being provided with X ray visible elements.

Figure 15:
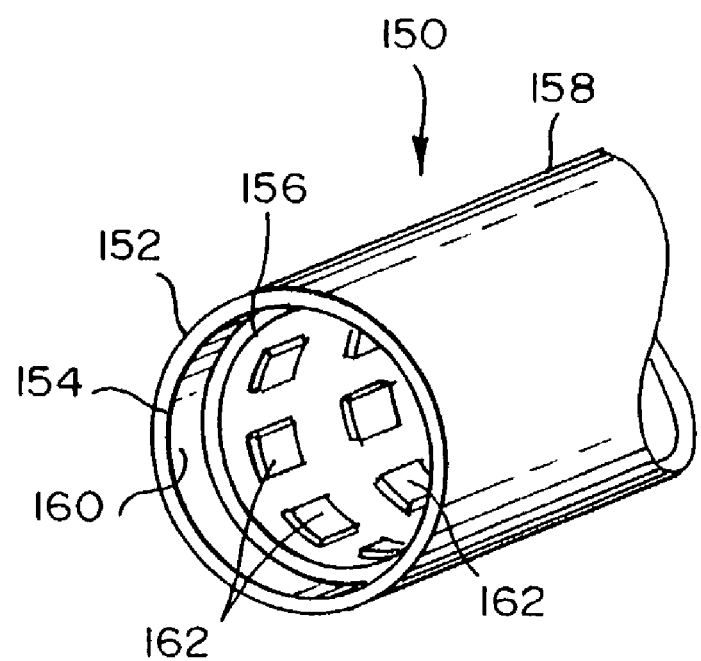
FIG. 15 is partial perspective view of a still further constriction device embodying the present invention.

FIG. 15 illustrates still another constriction device 150 embodying the present invention. Again, the device 150 is a generally cylindrical sleeve having opposed opened ends, one of which is shown at 152. The end 152 includes an integral compression rim 154. Spaced from the integral rim 154 is a proximal circumferential compression band 156. The band 156 may be integral to the device sidewall 158 or adhered to the inner surface 80 thereof. Spaced from and adjacent the band 156 and on the inner surface 160 of the sleeve are a plurality of fixation elements 162. The fixation elements are generally square shaped pads arranged in rows adjacent each other and circumscribing the inside of the cylindrical device 150. As in the previous embodiments, the fixation elements are closely spaced. The band 156 and fixation elements 162 form a fixation system. When the device 150 is expanded to receive the tissue to be constricted, the tissue at least partially fills the spaces between adjacent fixation elements 162. Then, when the device 150 is permitted to collapse about the tissue to be constricted, adjacent fixation elements 162 move toward each other to grasp the tissue and the proximal band 156 compresses the tissue to form a mechanical lock on the most distal compressed tissue. This again provides positive fixation of the device on the constricted tissue and serves to resist migration or movement of the device in a longitudinal direction to maintain the device in a fixed position on the tissue.

The fixation elements 162 may again be formed of an X ray opaque material such as gold or stainless steel, for example. Alternatively, the fixation elements 162 may be formed of flexible or elastic biocompatible material.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A method of permanently constricting lung tissue, the method comprising the steps of:
   exposing the thoracic cavity;
   radially expanding an elongated sleeve having an inner surface and opposed ends with one end being open for receiving the lung tissue;
   drawing the lung tissue to be constricted in the expanded sleeve;
   releasing the sleeve from the expanded condition to constrict the lung tissue therein, the sleeve being arranged to contract when released; and
   fixating a portion of the sleeve to the lung tissue with a plurality of fixation elements projecting inward of the inner surface that grasp the lung tissue upon release of the sleeve from the expanded condition.

2. The method of claim 1, wherein the elongated sleeve is arranged to elastically contract when released from the expanded condition.

3. The method of claim 1, wherein when the lung tissue is positioned in the expanded sleeve, the lung tissue at least partially fills a space between the fixation elements.

4. The method of claim 1, wherein when the sleeve is released from the expanded condition, the fixation elements move toward each other to grasp the lung tissue.

5. The method of claim 1, wherein the elongated sleeve comprises a radiopaque material.

6. The method of claim 5, wherein the radiopaque material comprises strips.

7. The method of claim 6, wherein the strips are longitudinally oriented along the inner surface of the elongated sleeve.

8. The method of claim 5, further comprising confirming the positioning of the sleeve through fluoroscopy.

9. The method of claim 1, wherein the fixation elements are substantially square shaped pads.

10. The method of claim 9, wherein the square shaped pads are arranged in a plurality of rows.

11. The method of claim 10, wherein the plurality of rows circumscribe one end of the elongated sleeve.

12. The method of claim 1, wherein the fixation elements are substantially elongated bars.

13. The method of claim 1, further comprising severing the elongated sleeve and constricted lung tissue.

* * * * *

UNITED STATES PATENT AND TRADEMARK OFFICE
CERTIFICATE OF CORRECTION

| | |
|---|---|
| PATENT NO. | : 7,182,772 B2 |
| APPLICATION NO. | : 10/287189 |
| DATED | : February 27, 2007 |
| INVENTOR(S) | : Alferness et al. |

It is certified that error appears in the above-identified patent and that said Letters Patent is hereby corrected as shown below:

In Sheet 4 of 6, Fig. 9, Line 1, left to "Fig. 9", please insert -- 124 --.

Signed and Sealed this

Tenth Day of July, 2007

JON W. DUDAS
*Director of the United States Patent and Trademark Office*